United States Patent
Byrne

(10) Patent No.: US 7,842,507 B1
(45) Date of Patent: Nov. 30, 2010

(54) SENSOR FOR DIRECT MEASUREMENT OF CARBONATE IONS IN SEAWATER

(75) Inventor: Robert H. Byrne, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 288 days.

(21) Appl. No.: 12/110,730

(22) Filed: Apr. 28, 2008

Related U.S. Application Data

(60) Provisional application No. 60/914,384, filed on Apr. 27, 2007.

(51) Int. Cl.
*G01N 33/00* (2006.01)
(52) U.S. Cl. .......................................... 436/133; 436/77
(58) Field of Classification Search ................. 436/133, 436/163, 171, 77
See application file for complete search history.

(56) References Cited

U.S. PATENT DOCUMENTS 5,001,070 A    3/1991   Ivaska et al.

FOREIGN PATENT DOCUMENTS

EP            0285628 B1    2/1992

OTHER PUBLICATIONS

Y. S. Fung, Zucheng Wu, and K. L. Dao. "Determination of Total Organic Carbon in Water by Thermal Combustion-Ion Chromatography." Anal. Chem. 68. 13. pp. 2186-2190. 1996.

Kendra L. Daly, Robert H. Byrne, Andrew G. Dickson, Scott M. Gallager, Mary Jane Perry, Margaret K. Tivey. "Chemical and Biological Sensors for Time-Series Research: Current Status and New Directions." Marine Technology Soc. Journal. vol. 38. No. 2. pp. 121-143. 2004.

Robert H. Byrne and William L. Miller. "Copper(II) carbonate complexation in Seawater." Geochimica et Cosmochimica Acta. vol. 49. No. 8. pp. 1837-1844. 1985.

(Continued)

*Primary Examiner*—Robert J Hill, Jr.
*Assistant Examiner*—Dwan A Gerido
(74) *Attorney, Agent, or Firm*—Michele L. Lawson; Michael M. McGaw; Smith & Hopen P.A.

(57) ABSTRACT

A system and associated methodology to directly measure the concentration of carbonate ions in seawater by ultraviolet absorbance spectroscopy. Metal ions are added to seawater and the absorbance spectra of the added ions are measured in the ultraviolet. The spectral absorbance (light attenuation) of ions such as divalent lead or copper in seawater is predominantly determined by the carbonate ion content of seawater. Through a knowledge of (1) the strength of association between carbonate and either divalent lead or divalent copper and (2) the spectral characteristics of these cations in seawater (e.g., $Pb^{2+}$ complexed solely as $PbCO_3$ and $Pb^{2+}$ complexed solely in the form of chloride complexes), it is possible to directly determine seawater carbonate ion concentrations from absorbance measurements at a variety of wavelengths in the ultraviolet. Using such procedures, carbonate ion concentrations can be directly measured, rather than calculated from other $CO_2$ system parameters such as pH and total dissolved inorganic carbon. Measurements of carbonate ion concentrations, and measurements of solution pH that also involve spectrophotometric procedures, will allow both types of measurements in a single, small, robust instrument. Furthermore, via simple thermodynamic calculations, conjugate measurements of carbonate and pH can then be used to calculate all carbon system parameters of interest, including the total concentration of dissolved inorganic carbon in seawater.

11 Claims, 12 Drawing Sheets

OTHER PUBLICATIONS

R. H. Byrne. "Inorganic lead complexation in natural seawater determind by UV spectroscopy." Nature. Vol. 290. No. 5806. pp. 487-489. 1981.

Tonya D. Clayton and Robert H. Byrne. "Spectrophotpmetric seawater pH measurements: total hydrogen ion concentration scale calibration of m-cresol purple and at-sea results." Deep-Sea Research/ vol. 40. No. 10. pp. 2115-2129. 1993.

SENSOR FOR DIRECT MEASUREMENT OF CARBONATE IONS IN SEAWATER

CROSS REFERENCE TO RELATED APPLICATIONS

This application claims priority to currently pending U.S. Provisional Patent Application 60/914,384, entitled, "Sensor for Direct Measurement of Carbonate Ions in Sea Water", filed Apr. 27, 2007, the contents of which are herein incorporated by reference.

FIELD OF INVENTION

This invention relates to sensors for deployment in saltwater environments. More specifically, this invention relates to sensors for the measurement of carbonate ions in seawater.

BACKGROUND OF THE INVENTION

Carbonate ion concentrations are important parameters in marine ecosystems. Investigations of the marine $CO_2$ system are commonly conducted through measurements of four primary variables: total dissolved inorganic carbon ($C_T$), total solution alkalinity ($A_T$), $CO_2$ fugacity ($f_{CO2}$), and solution pH. Thermodynamic models link these four primary variables, whereby measurements of any two variables can be used to calculate the two remaining parameters (DOE, 1994. Handbook of Methods, Version 2, A. G. Dickson & C. Goyet, eds. ORNL/CDIAC-74). These models also allow calculations of the concentrations of the individual forms of inorganic carbon in seawater: the dissolved concentrations of $CO_2$ and $H_2CO_3$, and the free plus ion paired concentrations of bicarbonate, $HCO_3^-$, and carbonate, $CO_3^{2-}$. Two of the directly measured and derived $CO_2$ system variables can be highlighted because of their special significance in evaluations of global carbon fluxes and the biogeochemistry of marine carbonates in general. $CO_2$ fugacity measurements are essential to descriptions of $CO_2$ exchange at the air sea interface (DOE, 1994; McGillis, W. R. and Wanninkhof, R.; *Mar. Chem.* 2006, 100-108; Millero, F. J. *Chem. Rev.* 2007, 107, 308-341), and carbonate ion concentrations are essential to evaluations of (a) the mineralization rates of marine calcifiers (Langdon, C. and Atkinson, M. J., *J Geophys. Res.* 2005, 110, C09S05, doi: 10.1 029/2004JC002576) and (b) the dissolution rates of calcite and aragonite ($CaCO_{3(S)}$ polymorphs) both on the seafloor and in the water column (Keir, R. S. *Geochim. Cosmochim. Acta.* 1980, 44, 241-252; Morse, J. W. *Amer. J. Sci.* 1978, 278, 344-355; Acker, J. G., et al., *Geochim. et Cosmochim. Acta* 1987, 51, 2171-2175). Rising atmospheric carbon dioxide concentrations over the past two centuries have led to increasing $CO_2$ uptake by the oceans (Royal Society, 2005, Ocean Acidification due to Increasing Atmospheric Carbon Dioxide. *Policy Document* 12/05, *The Royal Society*). This process, which is decreasing the pH of the upper ocean, is reducing oceanic carbonate ion concentrations and thus the level of saturation of calcium carbonate (Broecker, W. S., et al., *Science* 1979, 206, 409-418; Feely, R. A., et al., *Science.* 2004, 305, 362-366; Orr, J. C., et al., *Nature.* 2005, 437, 681-686). If the trend continues, it will have a seriously negative impact on key marine organisms such as corals and some plankton (Kleypas et al, Impacts of Acidification on Coral Reefs and Other Marine Calcifiers: A guide for Future Research. Report of a workshop held 18-20 Apr. 2005, St. Petersburg Fla., sponsored by NSF, NOAA and U.S. Geological Survey. 88 pp). In view of the importance of carbonate ion concentrations ($[CO_3^{2-}]_T$) to the oceans' rapidly evolving carbonate system, it is then highly desirable to move ($[CO_3^{2-}]_T$ from the rank of derived $CO_2$ system variables to the list of primary measured variables. The present invention provides methods and associated systems to meet this important objective.

SUMMARY OF INVENTION

The present invention provides procedures for measurement of carbonate ion concentrations in seawater by direct spectrophotometric observations of metal ion complexation (e.g. $Pb^{II}$). Metal ions are added to seawater and the absorbance spectra of the added ions are measured in the ultraviolet. The health of coral reefs and calcareous plankton is strongly influenced by the carbonate saturation state of seawater. Calculations of carbonate saturation states currently require measurements of two $CO_2$ system parameters, such as pH and total dissolved carbon, plus thermodynamic calculations that relate carbonate ion concentrations to directly measured parameters. The present invention provides novel procedures for direct measurements of carbonate ion concentrations and saturation states in seawater. The spectral absorbance (light attenuation) of ions, such as divalent lead or copper, in seawater is predominantly determined by the carbonate ion content of seawater.

Measurements are obtained via ultraviolet spectroscopic observations of $Pb^{II}$ spectra as the relative concentrations of $PbCO_3^{\circ}$ and an ensemble of lead chloride complexes vary in response to dissolved $CO_3^{2-}$. Measurement precision is enhanced by parameterization in terms of absorbance ratios. The $PbCO_3^{\circ}$ stability constant, and $Pb^{II}$ molar absorbance ratios in seawater, were determined at 25° C. over a range of salinity between 36 and 20. The procedures taught herein are well suited to measurements throughout the normal range of carbonate ion concentrations in the oceans. Rapid equilibration rates for $Pb^{II}$ carbonate complexation make the procedures described in this work well suited to rapid direct analysis in situ.

In a first aspect the present invention provides a method of measuring carbonate ion concentrations in seawater. The method includes the steps of adding a $Pb^{II}$ to a sample of the seawater to produce a sample solution, spectrophotometrically measuring the absorbance of light passing through the sample solution at a plurality of wavelengths and computing the carbonate ion concentration in seawater based upon the absorbance ratio of the sample solution at the plurality of wavelengths. The measured ultraviolet absorbance of light is a function of the complexation in the sample solution of the added $Pb^{II}$ with the carbonate ion of the seawater sample.

The spectrophotometric absorbance measurements can be obtained in the ultraviolet range. In certain embodiments of the method, one of the plurality spectrophotometric absorbance measurements used to calculate the absorbance ratio is measured at about $\lambda=234$ nm. Further embodiments utilize a second absorbance measurement of the plurality of spectrophotometric absorbance measurements used to calculate the absorbance ratio measured in the range of at about $\lambda=240$ nm. to about $\lambda=260$ nm. In additional embodiments the spectrophotometric absorbance measurements are measured at about $\lambda=234$ nm. and about $\lambda=250$ nm.

In a second aspect the present invention provides a method of measuring carbonate ion concentrations in an aqueous media. The method includes the steps of adding a metal ion species to a sample of the aqueous media to produce a sample solution, spectrophotometrically measuring the absorbance of light passing through the sample solution at a plurality of wavelengths and computing the carbonate ion concentration in aqueous media based upon the absorbance ratio of the sample solution at the plurality of wavelengths. The measured ultraviolet absorbance of light is a function of the complexation in the sample solution of the added metal ion species with the carbonate ion of the aqueous media.

In certain embodiments the added metal ion species can be a lanthanide metal, an actinide metal, Yttrium, $Pb^{II}$ or $Cu^{II}$. In this and other aspects the lanthanide metal can be selected from the group La, Ce, Pr, Nd, Pm, Sm, Eu, Gd, Tb, Dy, Ho, Er, Tm, Yb, and Lu. In certain aspects the actinide metal can be uranium. In an advantageous embodiment the metal ion species is $Pb^{II}$ and the absorbance measurements are obtained as absorbance ratios measured at about $\lambda=234$ and about $\lambda=250$. The aqueous media measured can be an aqueous media characterized by salinity. The salinity can be in the range of between about 20 and about 36. In an advantageous embodiment the aqueous media is seawater.

In a third aspect the present invention provides a method of measuring salinity in seawater. The method can include the steps of adding a metal ion species to a sample of the seawater to produce a sample solution, spectrophotometrically measuring the absorbance of light passing through the sample solution at a plurality of wavelengths and computing the salinity in the seawater media based upon the absorbance ratio of the sample solution at the plurality of wavelengths. The measured ultraviolet absorbance of light is a function of the complexation in the sample solution of the added metal ion species with carbonate ions of the seawater sample;

The spectrophotometric absorbance measurements can be obtained in the ultraviolet range. In certain embodiments the added metal ion species can be $Pb^{II}$ or $Cu^{II}$. In an advantageous embodiments the metal ion species is $Pb^{II}$ and the absorbance measurements are obtained as absorbance ratios measured at about $\lambda=234$ and about $\lambda=250$. In certain embodiments of the method, one of the plurality spectrophotometric absorbance measurements used to calculate the absorbance ratio is measured at about $\lambda=234$ nm. Further embodiments utilize a second absorbance measurement of the plurality of spectrophotometric absorbance measurements used to calculate the absorbance ratio measured in the range of at about $\lambda=240$ nm. to about $\lambda=260$ nm. In additional embodiments the spectrophotometric absorbance measurements are measured at about $\lambda=234$ nm. and about $\lambda=250$ nm.

In a fourth aspect the present invention provides an apparatus for measuring carbonate ion concentrations in seawater. The apparatus includes (i) a metal ion addition module for the addition of metal ion species to a sample of seawater and (ii) a spectrophotometric module for the spectrophotometric measurement of the attenuation of light passing through a resulting sample solution containing the added metal ion. The measured attenuation of light is a function of the carbonate ion concentration of the seawater sample.

In a fifth aspect the present invention provides a method of measuring salinity or chloride ion concentrations in an aqueous media. The method includes the steps of adding a metal ion species to a sample of the aqueous media to produce a sample solution, spectrophotometrically measuring the absorbance of light passing through the sample solution at a plurality of wavelengths and computing the salinity or chloride ion concentration in aqueous media based upon the absorbance ratio of the sample solution at the plurality of wavelengths. The measured ultraviolet absorbance of light is a function of the complexation in the sample solution of the added metal ion species with the carbonate ion of the aqueous media. In certain embodiments the added metal ion species can be a lanthanide metal, an actinide metal, Yttrium, $Pb^{II}$ or $Cu^{II}$.

In a sixth aspect the present invention provides an additional method of measuring carbonate ion, salinity or chloride ion concentrations in an aqueous media. The method includes the steps of adding a metal ion species to a sample of the aqueous media to produce a sample solution, spectrophotometrically measuring the fluorescence of light in a sample solution at a plurality of applied wavelengths and computing the carbonate ion, salinity or chloride ion concentration in aqueous media based upon the fluorescence ratio of the sample solution at the plurality of wavelengths. The measured ultraviolet absorbance of light is a function of the complexation in the sample solution of the added metal ion species with the carbonate ion of the aqueous media. As indicated more fully below, salinity and/or chloride ion concentration are found to vary in accordance with the complexation of carbonate ions with the added metal ion species. In certain embodiments the added metal ion species can be a lanthanide metal, an actinide metal, Yttrium, $Pb^{II}$ or $Cu^{II}$.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
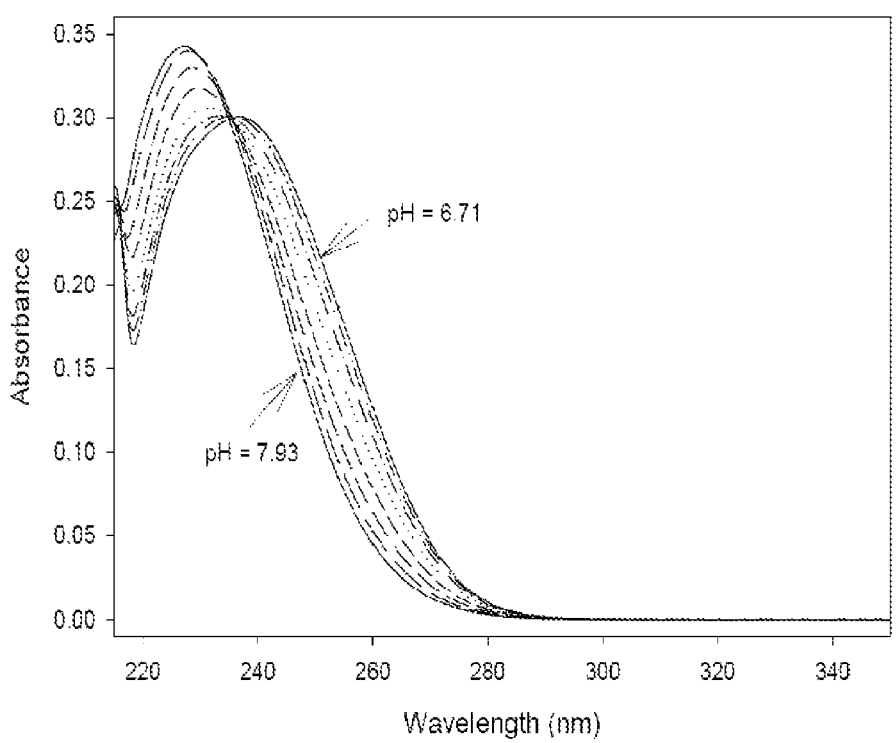
FIG. 1 is a graph showing the $Pb^{II}$ UV absorbance spectra in seawater at S 35.87 and 25° C. as a function of pH.

The present invention provides procedures for measurement of carbonate ion concentrations in seawater by direct spectrophotometric observations of $Pb^{II}$ complexation. The health of coral reefs and calcareous plankton is strongly influenced by the carbonate saturation state of seawater. Calculations of carbonate saturation states currently require measurements of two $CO_2$ system parameters, such as pH and total dissolved carbon, plus thermodynamic calculations that relate carbonate ion concentrations to directly measured parameters. The present invention provides novel procedures for direct measurements of carbonate ion concentrations and saturation states in seawater. Measurements are obtained via ultraviolet spectroscopic observations of $Pb^{II}$ spectra as the relative concentrations of $PbCO_3^0$ and an ensemble of lead chloride complexes vary in response to dissolved $CO_3^{2-}$. Measurement precision is enhanced by parameterization in terms of absorbance ratios. The $PbCO_3^0$ stability constant, and $Pb^{II}$ molar absorbance ratios in seawater, were determined at 25° C. over a range of salinity between 36 and 20. The procedures taught herein are well suited to measurements throughout the normal range of carbonate ion concentrations in the oceans. Rapid equilibration rates for $Pb^{II}$ carbonate complexation make the procedures described in this work well suited to rapid direct analysis in situ.

A variety of metals in seawater, including lead (Byrne, R. H. Nature 1981, 290, 487-489), copper (Byrne, R. H. and Miller W. L. Geochim. et Cosmochim. Acta 1985, 49, 1837-1844), Yttrium, the lanthanides (Cantrell, K. J. and Byrne R. H. Geochim. et Cosmochim. Acta 1987, 51, 597-605) and various actinides (Byrne, R. H. Geochem. Trans. 2002, 3, 11-16) have inorganic speciation schemes that are strongly dominated by carbonate complexation. It is envisioned that these metals from these groups (i.e. Yttrium and rare earth metals—lanthanides ($La^{III}$, $Ce^{III}$, ... through $Lu^{III}$) and actinides; with respect to actinides it is envisioned that uranium would be a preferable metal species to employ) could perform as substitutes for lead or copper in the methodology. Among these metals, the speciation of $Pb^{II}$ and $Cu^{II}$ has been examined directly by ultraviolet absorbance spectroscopy in natural seawater (Byrne, 1981; Byrne and Miller, 1985). Since ultraviolet absorbance spectra are strongly influenced by the carbonate ion concentration of seawater, it follows that observations of $Pb^{II}$ and $Cu^{II}$ absorbance spectra can be used to directly determine seawater carbonate ion concentrations. As a means of achieving high precisions in such determinations, procedures have been developed that involve measurements of absorbance ratios rather than absolute absorbance. The techniques applied can be compared and contrasted with those for seawater pH measurements, which achieve precisions on the order of 0.0004 pH units (Robert-Baldo, G. et al. Anal. Chem. 1985, 57, 2564-2567; Byrne, R. H. Anal. Chem. 1987, 59, 1479-1481; Byrne, R. H. and Breland, J. A. Deep-Sea Res. A. 1989, 36, 803-810; Clayton, T. D. and Byrne, R. H. Deep-Sea Res. A. 1993, 40:2115-2129). Whereas spectrophotometric observations of sulfonphthalein acid/base equilibria are utilized for seawater pH measurements, spectrophotometric observations of metal ion complexation can be used to quantify anion concentrations in seawater. Lead is especially well suited to such measurements because (a) $PbCO_3^0$ and a variety of $Pb^{II}$ chloride complexes have dissimilar absorbance spectra in the ultraviolet, and (b) species other than $PbCO_3^0$ and chloride complexes appear to be insignificant over a wide range of salinities in natural seawater. In this work, $Pb^{II}$ formation constants and molar absorbance ratios required for direct determinations of carbonate ion concentrations in seawater are characterized at 25° C. as a function of salinity. In addition to development of procedures for measurement of carbonate ions and carbonate saturation state, it is shown herein that measurements of $Pb^{II}$ absorbance ratios in acidified seawater can be used to determine seawater salinity with a precision on the order of ±0.1 salinity units. As an alternative to measuring absorbance, measurements of fluorescence could be employed to determine carbonate ion concentrations, salinity or chloride ion concentration. It is further envisioned that fluorescence measurements could be compared as fluorescence ratios to perform the calculations to determine parameters such as concentration. The procedures described in this work are suitable for rapid autonomous in-situ monitoring of carbonate ion concentration in seawater.

Theoretical Description

The $PbCO_3^0$ formation reaction in seawater, $$(Pb^{2+})_T + (CO_3^{2-})_T \leftrightarrow (PbCO_3^0)_T, \quad (1)$$

can be quantitatively described with an equilibrium constant of the following form:

$$CO3\beta1 = \frac{[PbCO_3^0]_T}{[Pb_T][CO_3^{2-}]_{T}} \quad (2)$$

where $[Pb_T]$ represents the total concentration of Pb(II) species other than $PbCO_3^0$ in seawater, principally $Pb^{2+}$, $PbCl^+$, $PbCl_2^0$ and $PbCl_3^-$ and minor amounts of $PbSO_4^0$; $[CO_3^{2-}]_T$ is the sum concentration of free and ion paired carbonate ($CO_3^{2-}$, $NaCO_3^-$, $MgCO_3^0$ and $CaCO_3^0$); and $[PbCO_3^0]_T$ represents the sum concentration of $PbCO_3^0$ and potentially significant mixed ligand complexes such as $PbCO_3^0Cl^-$. The absorbance of $Pb^{II}$ in seawater can be described using the following equation (Byrne, 1981; Soli, A. L. et al. Mar. Chem. 2008, (in-press)):

$$_\lambda A = (_\lambda\epsilon_{Pb} + _\lambda\epsilon_{PbCO3} {}_{CO3}\beta_1 [CO_3^{2-}]_T)/(1 + {}_{CO3}\beta_1 [CO_3^{2-}]_T) \quad (3)$$

where $_\lambda A$ is the absorbance of $Pb^{II}$ at wavelength $\lambda$, $_\lambda\epsilon_{PbCO3}$ is the molar absorbance of $(PbCO_3^0)_T$ at wavelength $\lambda$, $_\lambda\epsilon_{Pb}$ is the molar absorbance of $(Pb)_T$ at wavelength $\lambda$ and $_{CO3}\beta_1$ is the formation constant of $PbCO_3^0$ as defined in equation (2). Equation (3) can be used to describe the dependence of $Pb^{II}$ absorbance data ($_\lambda A$) on $[CO_3^{2-}]_T$ and determine an internally consistent set of values for $_\lambda\epsilon_{Pb}$, $_\lambda\epsilon_{PbCO3}$ and $_{CO3}\beta_1$.

Use of equation (3) at wavelengths and allows carbonate ion concentrations, $[CO_3^{2-}]_T$, to be directly calculated from observations of absorbance ratios:

$$R = {}_{\lambda 2}A/{}_{\lambda 1}A = ({}_{\lambda 2}\epsilon_{Pb} + {}_{\lambda 2}\epsilon_{PbCO3} {}_{CO3}\beta_1 [CO_3^{2-}])/({}_{\lambda 1}\epsilon_{PbCO3} {}_{CO3}\beta_1 [CO_3^{2-}]) \quad (4)$$

Rearrangement of equation (4) results in the following equation:

$$-\log [CO_3^{2-}] = \log {}_{CO3}\beta_1 + \log((R-e_1)/(e_2 - R \cdot e_3)) \quad (5)$$

where $e_1$, $e_2$, and $e_3$ are $Pb^{II}$ molar absorbance ratios:

$$e_1 = {}_{\lambda 2}\epsilon_{PbCO3}/{}_{\lambda 1}\epsilon_{PbCO3}, \quad e_2 = {}_{\lambda 2}\epsilon_{Pb}/{}_{\lambda 1}\epsilon_{PbCO3}, \quad e_3 = {}_{\lambda 1}\epsilon_{Pb}/{}_{\lambda 1}\epsilon_{PbCO3} \quad (6)$$

The form of equation (5) is analogous to that which has been used for highly precise measurements of seawater pH from observations of sulfonephthalein absorbance in seawater (Robert-Baldo et al, 1985; Byrne, 1987; Byrne and Breland, 1989; Clayton and Byrne, 1993).

At sufficiently low pH, equation (4) can be written as:

$$R = {}_{\lambda 2}A/{}_{\lambda 1}A = {}_{\lambda 2}\epsilon_{Pb}/{}_{\lambda 1}\epsilon_{Pb} \quad (7)$$

Characterizations of the molar absorptivities of individual species of $Pb^{II}$ can be used to directly determine the relative concentrations of $Pb^{2+}$, $PbCl^+$, $PbCl_2^0$ and $PbCl_3^-$ in both synthetic solutions and seawater. Since the relative concentrations of these species are directly dependent on the chloride concentrations in synthetic solutions and seawater, it follows that $Pb^{II}$ absorbance ratios at low pH are directly dependent on salinity. In addition to developing a direct means of determining carbonate ion concentrations via equation (5), it is shown herein that observations of $Pb^{II}$ absorbance ratios at low pH allow calculations of seawater salinity with a precision somewhat better than ±0.2%.

Methods and Procedures

Equation (5) can be used to determine carbonate ion concentrations via direct measurements of $Pb^{II}$ absorbance ratios, and characterizations of $_{CO3}\beta_1$, $e_1$, $e_2$, and $e_3$. Observations of $Pb^{II}$ absorbance spectra at salinities typical of open ocean seawater (S=35.87) reveal isosbestic points near 234 nm (FIG. 1). On this basis, one of the two wavelengths chosen for absorbance observations was $\lambda_1$=234 nm. Although use of shorter wavelengths is desirable as a means of increasing sensitivity to formation of $PbCO_3^0$, small absorbance contributions from carbonate ions at shorter wavelengths make interpretations of absorbances at $\lambda$<234 nm less direct. In view of the substantial absorbance variations between 240 and 260 nm (FIG. 1), the second of the two wavelengths chosen for absorbance ratio observations was $\lambda_2$=250 nm.

Figure 2:
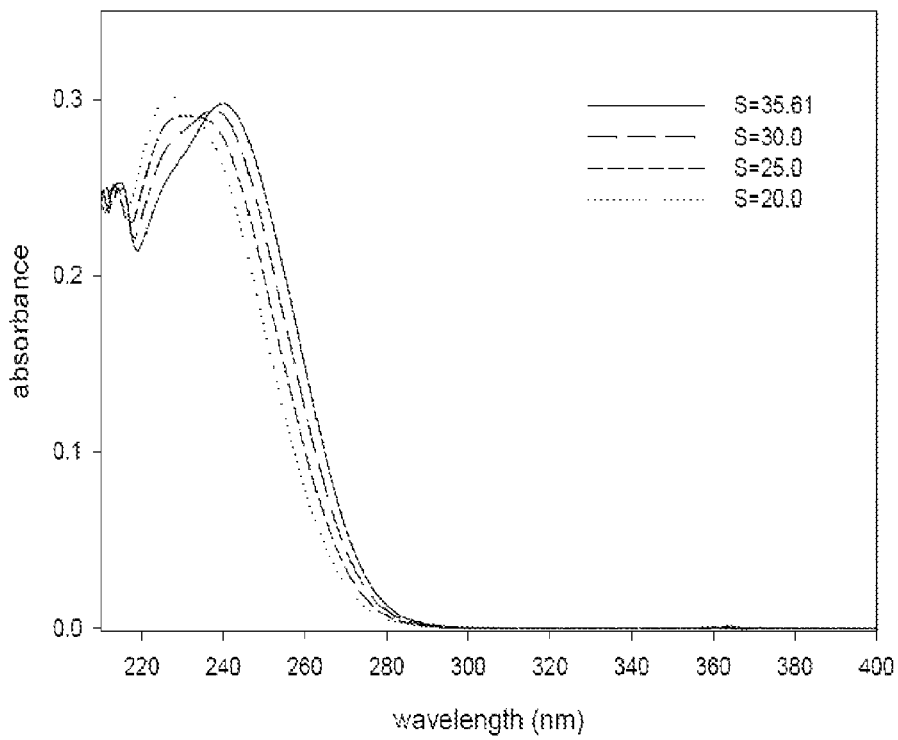
FIG. 2 is a graph showing the $Pb^{II}$ UV absorbance spectra of acidified seawater (25° C., pH=3.73) at four selected salinities.

Measurements of log $_{CO3}\beta_1$ in this work were obtained using equation (3) and observations of $_{250}A$ and $[CO_3^{2-}]_T$ in seawater samples at constant salinity and constant temperature. Along with measurements of log $_{CO3}\beta_1$, these measurements also produced paired characterizations of $_{250}\epsilon_{Pb}$ and $_{250}\epsilon_{Pb\ CO3}$. Paired characterizations of $_{234}\epsilon_{Pb}$ and $_{234}\epsilon_{Pb\ CO3}$ were obtained from measurements of $_{234}A$ and $[CO_3^{2-}]_T$ using equation (3), and the log $_{CO3}\beta_{11}$ values determ $_{234}\epsilon_{Pb}$ and $_{250}\epsilon_{Pb}$ were obtained from $_\lambda A$ observations at low pH (FIG. 2). The molar absorbance ratios $e_1$, $e_2$, and $e_3$ in equation (5) were then determined from these paired molar absorbance characterizations as follows:

$$e_1 = (_{250}\epsilon_{PbCO3}/_{250}\epsilon_{Pb}) \times (_{234}\epsilon_{Pb}/_{234}\epsilon_{PbCO3}) \times (_{250}\epsilon_{Pb}/_{234}\epsilon_{Pb}) \quad (8)$$

$$e_2 = (_{234}\epsilon_{Pb}/_{234}\epsilon_{PbCO3}) \times (_{250}\epsilon_{Pb}/_{234}\epsilon_{Pb}) \quad (9)$$

$$e_3 = (_{234}\epsilon_{Pb}/_{234}\epsilon_{PbCO3}) \quad (10)$$

All chemicals used were analytical reagent grade. $PbCl_2$ and $NaHCO_3$ were from Sigma-Aldrich. HCl (1.000 M) was from J. T. Baker. The seawater used in this study was collected from the Gulf of Mexico. Seawater salinity was measured with an SBE 49 CTD (Seabird). Seawater samples at various salinities were prepared by dilution with Milli-Q water. Absorbance measurements were obtained using quartz optical cells in an HP 8453 spectrophotometer. The temperature of the samples in the optical cells was controlled (25±0.05)° C. with a Neslab refrigerating circulator and a water-jacketed spectrophotometric cell holder.

Seawater alkalinity was determined using the spectrophotometric method of Yao and Byrne (1998) which is precise to better than 1 µmol/kg. Seawater (140.0 g) was added gravimetrically to an open top optical cell which, in turn, was positioned in the thermostated cell holder. Sample pH was measured using an Orion Ross-type pH electrode (No. 800500) connected to an Orion pH meter (Model 720A) in the absolute millivolt mode. Nerstian behavior of the pH electrode was confirmed via titrations of 0.7 molal NaCl solutions with concentrated HCl. The electrode was calibrated on the total hydrogen ion concentration scale through measurements in natural seawater whose pH was determined by simultaneous spectrophotometric observations of thymol blue absorbance ratios (Zhang and Byrne, 1996).

Through addition of $NaHCO_3$, the alkalinity of each seawater sample was increased to values approximately double those of natural seawater (final alkalinity ~4.0 millimolal). After each seawater sample was thermally equilibrated, a reference spectrum was taken and 1.05 ml of a 0.001 mol/kg $PbCl_2$ stock solution was added to the sample (final $[Pb^{II}]_T$~7.5 µmol $kg^{-1}$). An absorbance spectrum was then taken along with a potentiometric measurement of pH. The sample was subsequently titrated with standard HCl using a Gilmont micrometer syringe. HCl additions were quantified gravimetrically. $Pb^{II}$ absorbance, alkalinity and pH were recorded for each titration point. Sample alkalinity was calculated by accounting $[CO_3^{2-}]_T$ from alkalinity and pH utilized the total $H^+$ scale dissociation constants of Dickson and Millero (1987) that were derived from the data of Mehrbach et al. (1973). Non-linear least squares parameter estimates of $_{\lambda 2}\epsilon_{Pb}$, $_{\lambda 2}\epsilon_{PbCO3}$ and $_{CO3}\beta_1$ were obtained using equation (3) and paired values of $_\lambda A$ and $[CO_3^{2-}]_T$. Calculations of $[CO_3^{2-}]_T$ that accounted for minor contributions of $PbCO_3^0$ to carbonate alkalinity did not cause significant changes in derived values of $_{\lambda 2}\epsilon_{Pb}$, $_{\lambda 2}\epsilon_{PbCO3}$ and $_{CO3}\beta_1$.

Absorbance contributions of $CO_3^{2-}$ at short wavelengths were examined by performing titration experiments without addition of $Pb^{II}$ to samples. Observations of well defined isosbestic points at $\lambda$=234 nm demonstrate that these corrections are very small at the wavelengths utilized in this work. The dependence $e_1$, $e_2$, and $e_3$ on salinity were described via quadratic functions.

$Pb^{II}$ absorbance measurements in acidified seawater (pH~3.7, $[Pb]_T$~7.5 µmol $kg^{-1}$) were used to determine $_\lambda \epsilon_{Pb}$ values at $\lambda$=234 and 250 nm. Absorbances, in this case, were measured against a reference solution of acidified seawater that contained no lead. The absorbance ratios obtained in these experiments ($_{250}\epsilon_{Pb}/_{234}\epsilon_{Pb}$) were used in determinations of $e_1$ and $e_2$ as described above, and were also used in a least squares quadratic regression that allows salinity (S) to be calculated from $_{234}A/_{250}A$ observations at low pH.

Example 1

Salinity Dependencies of $Pb^{II}$ Molar Absorptivities and the $PbCO_3^0$ Formation Constant

TABLE 1

$PbCO_3^0$ formation constant ($_{CO3}\beta_1$), $_{250}\epsilon_{Pb}$, and $_{250}\epsilon_{PbCO3}$ as a function of salinity at 25° C.

| Salinity | log $_{CO3}\beta_1$ | $_{250}\epsilon_{Pb}$ | $_{250}\epsilon_{PbCO3}$ |
|---|---|---|---|
| 35.87 | 4.070 ± 0.030 | 0.2584 ± 0.0021 | 0.0900 ± 0.0021 |
| 34.50 | 4.140 ± 0.028 | 0.2504 ± 0.0026 | 0.0973 ± 0.0018 |
| 32.50 | 4.151 ± 0.026 | 0.2382 ± 0.0021 | 0.0895 ± 0.0019 |
| 30.00 | 4.249 ± 0.021 | 0.2259 ± 0.0016 | 0.0875 ± 0.0014 |
| 27.50 | 4.290 ± 0.024 | 0.2175 ± 0.0021 | 0.0770 ± 0.0014 |
| 25.00 | 4.443 ± 0.028 | 0.2027 ± 0.0024 | 0.0768 ± 0.0013 |
| 22.50 | 4.559 ± 0.018 | 0.1841 ± 0.0015 | 0.0732 ± 0.0006 |
| 20.00 | 4.711 ± 0.022 | 0.1697 ± 0.0016 | 0.0674 ± 0.0008 |

Figure 3:
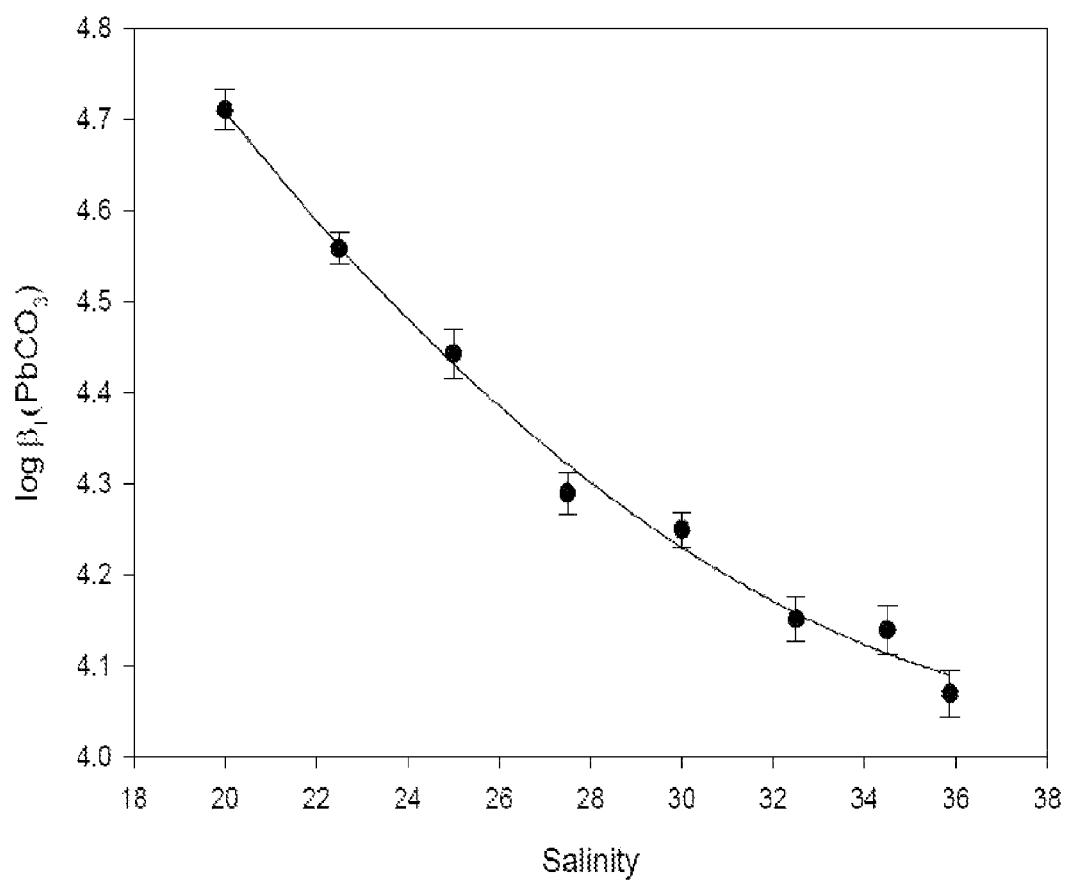
FIG. 3 is a graph showing salinity dependence of $PbCO_3^0$ formation constant at 25° C.
Figure 4:
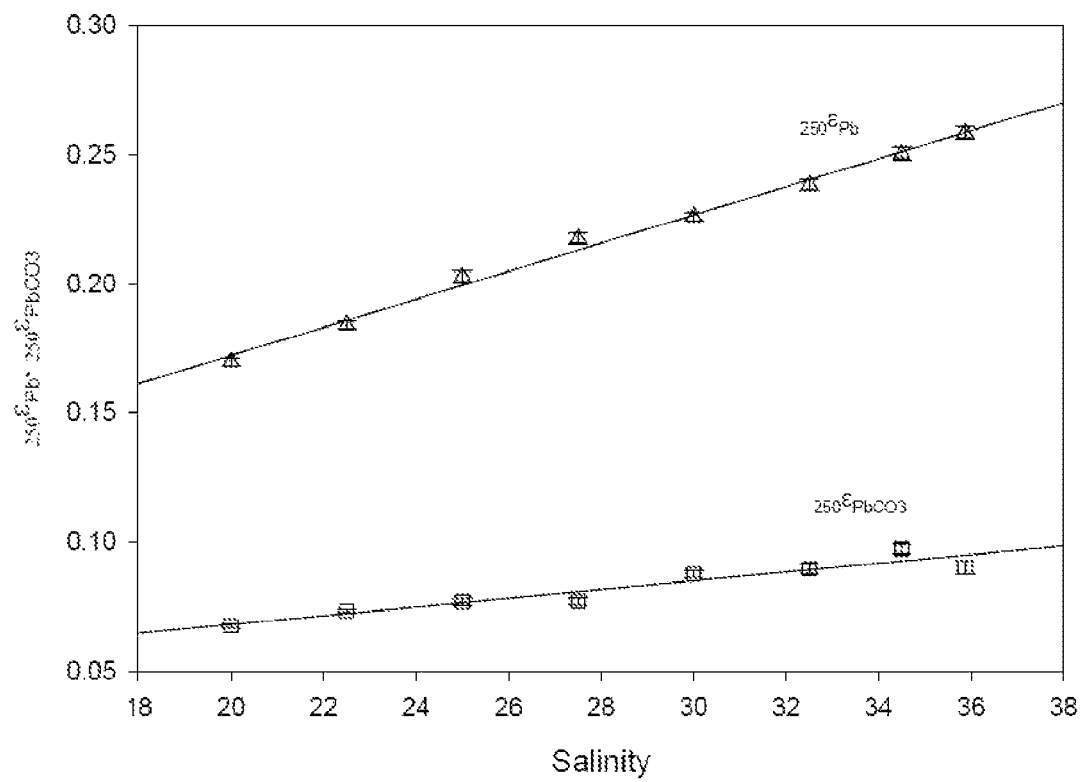
FIG. 4 is a graph showing salinity dependence of $_{250}\epsilon_{Pb}$ and $_{250}\epsilon_{PbCO3}$ at 25° C.

Estimates for $_{CO3}\beta_1$, $_{250}\epsilon_{Pb}$ and $_{250}\epsilon_{Pb\ CO3}$ obtained using equation (3) are given in Table 1 and are shown graphically in FIGS. 3 and 4. Over a salinity range between S=20 and S=36, the dependence of the $PbCO_3^0$ formation constant on S at 25° C. (FIG. 3) can be described as:

$$\log\ _{CO3}\beta_1 = 6.574 - 0.1235S + 1.514 \times 10^{-3}S^2 \quad (11)$$

with a ±0.023 standard error of estimation. The $_{250}\epsilon_{Pb}$ and $_{250}\epsilon_{PbCO3}$ values determined in this analysis exhibited a linear dependence on salinity:

$$_{250}\epsilon_{Pb} = 0.0632 + 5.446 \times 10^{-3}S \quad (12)$$

$$_{250}\epsilon_{Pb\ CO3} = 0.0342 + 1.692 \times 10^{-3}S \quad (13)$$

TABLE 2

$_{234}\epsilon_{Pb}$ and $_{234}\epsilon_{PbCO3}$ as a function of salinity at 25° C.

| Salinity | $_{234}\epsilon_{Pb}$ | $_{234}\epsilon_{PbCO3}$ |
|---|---|---|
| 35.87 | 0.2928 ± 0.0141 | 0.3210 ± 0.0022 |
| 34.50 | 0.2911 ± 0.0116 | 0.3190 ± 0.0026 |
| 32.50 | 0.2894 ± 0.0128 | 0.3191 ± 0.0006 |
| 30.00 | 0.2904 ± 0.0097 | 0.3101 ± 0.0005 |
| 27.50 | 0.2969 ± 0.0115 | 0.2924 ± 0.0009 |
| 25.00 | 0.2954 ± 0.0111 | 0.2819 ± 0.0012 |
| 22.50 | 0.2886 ± 0.0057 | 0.2696 ± 0.0022 |
| 20.00 | 0.2874 ± 0.0078 | 0.2511 ± 0.0035 |

Figure 5:
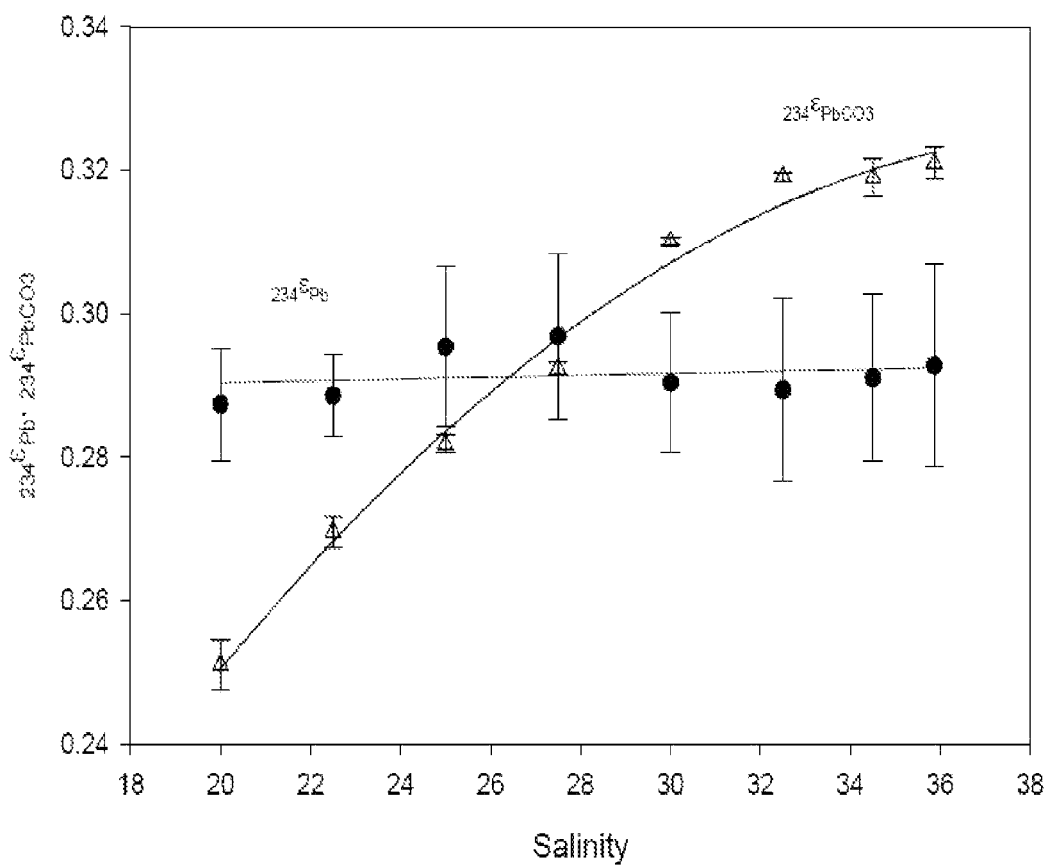
FIG. 5 is a graph showing salinity dependence of $_{234}\epsilon_{Pb}$ and $_{234}\epsilon_{PbCO3}$ at 25° C.

The $_{234}\epsilon_{Pb}$ and $_{234}\epsilon_{PbCO3}$ values determined using the log $_{CO3}\beta_1$ results in Table 1 and absorbance observations at 234 nm are given in Table 2. The FIG. 5 graphical depiction of these results shows that the dependence of $_{234}\epsilon_{Pb}$ on salinity is linear while satisfactory descriptions of $_{234}\epsilon_{PbCO3}$ require a quadratic term:

$$_{234}\epsilon_{Pb} = 0.2877 + 1.319 \times 10^{-4} S \quad (14)$$

$$_{234}\epsilon_{PbCO3} = 0.0232 + 1.518 \times 10^{-2} S - 1.906 \times 10^{-4} S^2 \quad (15)$$

Figure 6:
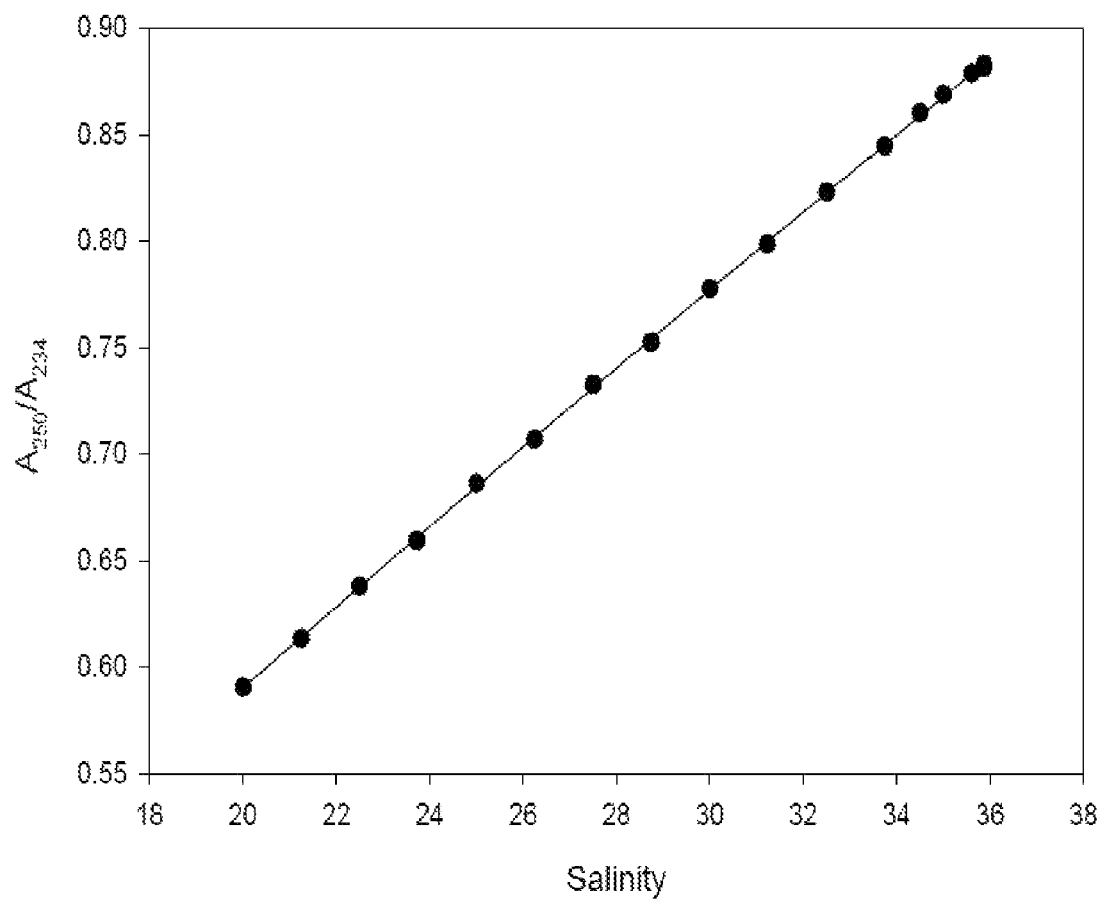
FIG. 6 is a graph showing the absorbance ratio of $Pb^{II}$ in acidified seawater at 234 and 250 nm: $_{250}A/_{234}A$ ($_{250}\epsilon_{Pb}/_{234}\epsilon_{Pb}$) as a function of salinity.

The salinity dependence for observations of ($_{250}\epsilon_{Pb}/_{234}\epsilon_{Pb}$) in acidified seawater (Table 3 and FIG. 6) is well described by the following expression:

$$_{250}\epsilon_{Pb}/_{234}\epsilon_{Pb} = 0.1931 + 1.062 \times 10^{-2} S - 3.852 \times 10^{-5} S^2 \quad (16)$$

TABLE 3

Absorbance of $Pb^{II}$ in acidified seawater (pH = 3.73): $_{250}A/_{234}A$ ($_{250}\epsilon_{Pb}/_{234}\epsilon_{Pb}$) as a function of salinity at 25° C.

| Salinity | $_{250}A/_{234}A$ ($_{250}\epsilon_{Pb}/_{234}\epsilon_{Pb}$) |
|---|---|
| 20.00 | 0.5906 |
| 21.25 | 0.6135 |
| 22.50 | 0.6308 |
| 23.73 | 0.6593 |
| 25.00 | 0.6863 |
| 26.25 | 0.7069 |
| 27.50 | 0.7327 |
| 28.75 | 0.7526 |
| 30.00 | 0.7778 |
| 31.24 | 0.7987 |
| 32.50 | 0.8231 |
| 33.75 | 0.8448 |
| 34.50 | 0.8603 |
| 35.00 | 0.8688 |
| 35.61 | 0.8788 |
| 35.87 | 0.8830 |
| 35.87 | 0.8818 |

Using the results that are summarized in equations (12) through (16), equations (8) through (10) can be used to calculate $e_1$, $e_2$, and $e_3$ at each salinity. The coefficients obtained in this manner are given in Table 4 and are depicted graphically in FIGS. (7), (8) and (9).

The salinity dependencies of $e_1$, $e_2$, and $e_3$ are then given as follows:

$$e_1 = 0.3447 - 6.662 \times 10^{-3} S + 1.463 \times 10^{-4} S^2 \quad (17)$$

$$e_2 = 0.7749 - 1.122 \times 10^{-2} S + 3.331 \times 10^{-4} S^2 \quad (18)$$

$$e_3 = 2.114 - 6.600 \times 10^{-2} S + 9.036 \times 10^{-4} S^2 \quad (19)$$

TABLE 4

$e_1$ ($_{250}\epsilon_{Pb\,CO3}/_{234}\epsilon_{Pb\,CO3}$), $e_2$ ($_{250}\epsilon_{Pb}/_{234}\epsilon_{Pb\,CO3}$), and $e_3$ ($_{234}\epsilon_{Pb}/_{234}\epsilon_{Pb\,CO3}$) as a function of salinity at 25° C.

| Salinity | $e_1$ | $e_2$ | $e_3$ |
|---|---|---|---|
| 35.87 | 0.2938 | 0.8009 | 0.9068 |
| 34.50 | 0.2890 | 0.7841 | 0.9131 |
| 32.50 | 0.2828 | 0.7619 | 0.9263 |
| 30.00 | 0.2766 | 0.7381 | 0.9498 |
| 27.50 | 0.2721 | 0.7182 | 0.9825 |
| 25.00 | 0.2694 | 0.7024 | 1.0262 |
| 22.50 | 0.2687 | 0.6908 | 1.0835 |
| 20.00 | 0.2701 | 0.6838 | 1.1588 |

Example 2

Determinations of $CO_3^{2-}$ Concentrations in Seawater

Equations (5), (11), and (17) through (19) permit direct measurements of $[CO_3^{2-}]_T$ from measurements of $Pb^{II}$ ratios in seawater at 25° C. Equation (5) can, however, also be written in an alternative form, with a smaller number of parameters:

$$-\log\ [CO_3^{2-}]_T = \log\ \{(_{CO3}\beta_1)/(e_2)\} + \log\ \{(R-e_1)/(1-Re_3/e_2)\} \quad (20)$$

Figure 10:
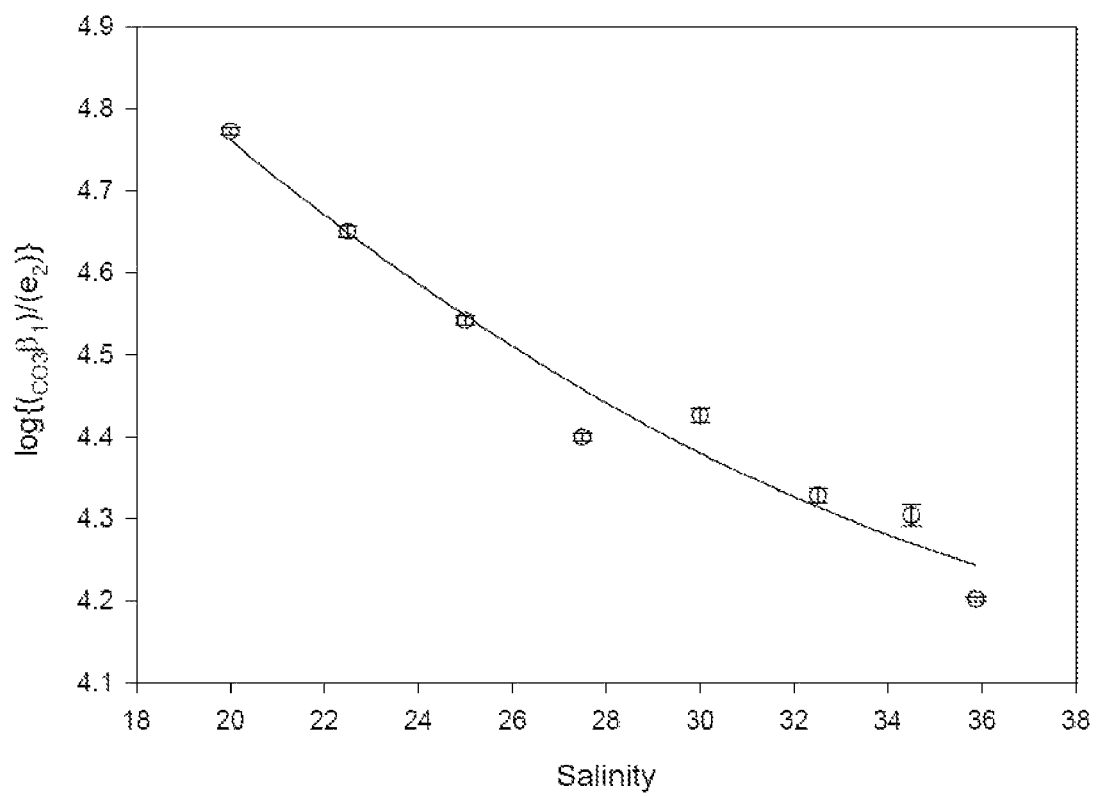
FIG. 10 is a graph showing the results obtained for log $\{(_{CO3}\beta_1)/(e_2)\}$ using equation (20).
Figure 11:
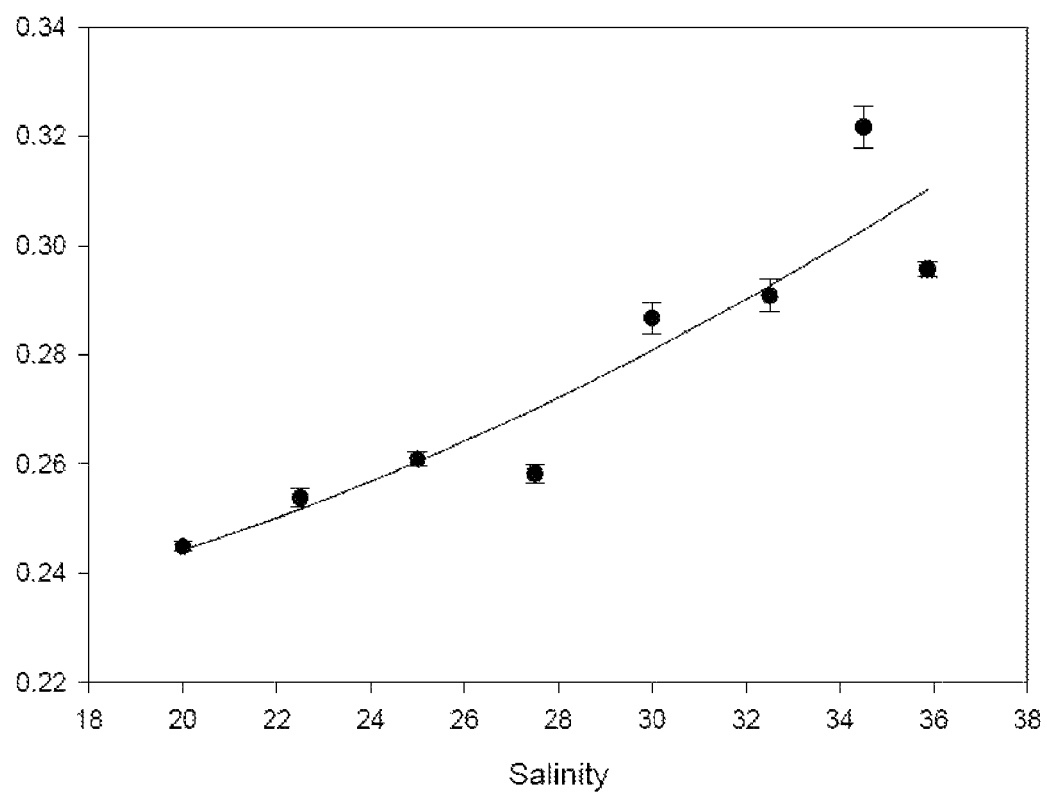
FIG. 11 is a graph showing the results obtained for $e_1$ using equation (20).
Figure 12:
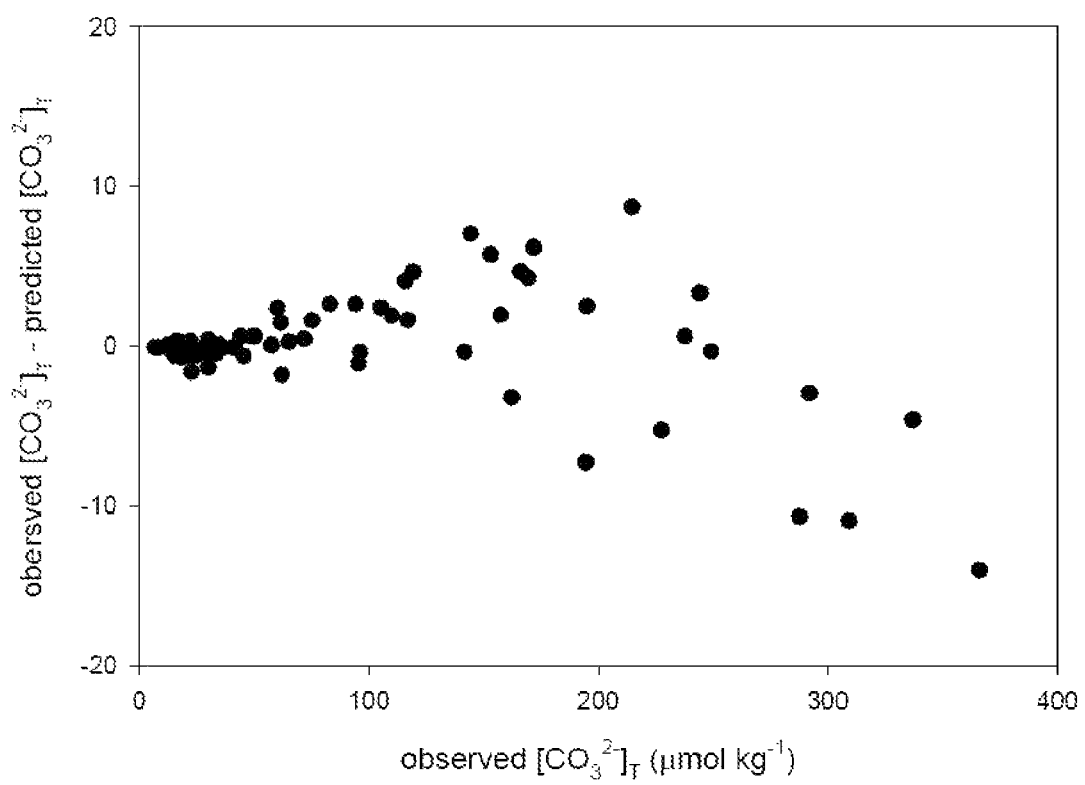
FIG. 12 is a graph showing the residuals ($[CO_3^{2-}]_{observed}-[CO_3^{2-}]_{predicted}$) plotted as a function of $[CO_3^{2-}]_{observed}$ for the least squares analyses using equation (20).

This equation is advantageous for calculations of carbonate ion concentrations because (a) it reduces the number of parameterizations required for measurements: Using equation (20), $(_{CO3}\beta_{11})/(e_2)$ is determined as a single parameter, and $(e_3/e_2)$ is determined as one parameter; (b) the parameter $(e_3/e_2)$ can be precisely determined from direct measurements at low pH: It is directly determined from the absorbance ratios shown in FIGS. 7-9 (($e_3/e_2$)=($_{250}A/_{234}A$)$^{-1}$); (c) using ($e_3/e_2$) values determined at low pH, equation (20) can be used with paired $[CO_3^{2-}]_T$ and R observations to directly determine $(_{CO3}\beta_{11})/(e_2)$ and $e_1$. The results of such analyses, using each of the data sets that were employed to develop equations (11) and (17) through (19) are given in Table 5 and are depicted graphically in FIGS. 10 and 11. FIG. 12 shows the residuals, $([CO_3^{2-}]_T)_{observed} - ([CO_3^{2-}]_T)_{predicted}$, for each least squares analysis using equation (20). These results show that equation (20) can be used to satisfactorily predict $[CO_3^{2-}]_T$ over a wide range of conditions in seawater. The best least squares descriptions for the salinity dependencies of the parameters in equation (20) for $20 \leq S \leq 36$ are given as follows:

$$\log\ \{(_{CO3}\beta_1)/(e_2)\} = 6.087 - 8.495 \times 10^{-2} S + 9.360 \times 10^{-4} S^2 \quad (21)$$

$$e_1 = 0.2215 - 5.554 \times 10^{-4} S + 8.440 \times 10^{-5} S^2 \quad (22)$$

$$(e_3/e_2) = 3.061 - 8.730 \times 10^{-2} S + 9.363 \times 10^{-2} S^2 \quad (23)$$

TABLE 5

Obtained log$\{(_{CO3}\beta_1)/(e_2)\}$ and $e_1$ using equation (20). ($e_3/e_2$) used in equation (20) is the reciprocal of $_{250}A/_{234}A$ listed in Table 3.

| Salinity | log$\{(_{CO3}\beta_{11})/(e_2)\}$ | $e_1$ |
|---|---|---|
| 35.87 | 4.202 | 0.2957 |
| 34.50 | 4.304 | 0.3217 |
| 32.50 | 4.328 | 0.2909 |
| 30.00 | 4.426 | 0.2867 |
| 27.50 | 4.400 | 0.2582 |
| 25.00 | 4.542 | 0.2609 |
| 22.50 | 4.650 | 0.2538 |
| 20.00 | 4.773 | 0.2449 |

Example 3

Determinations of Seawater Salinity

Figure 7:
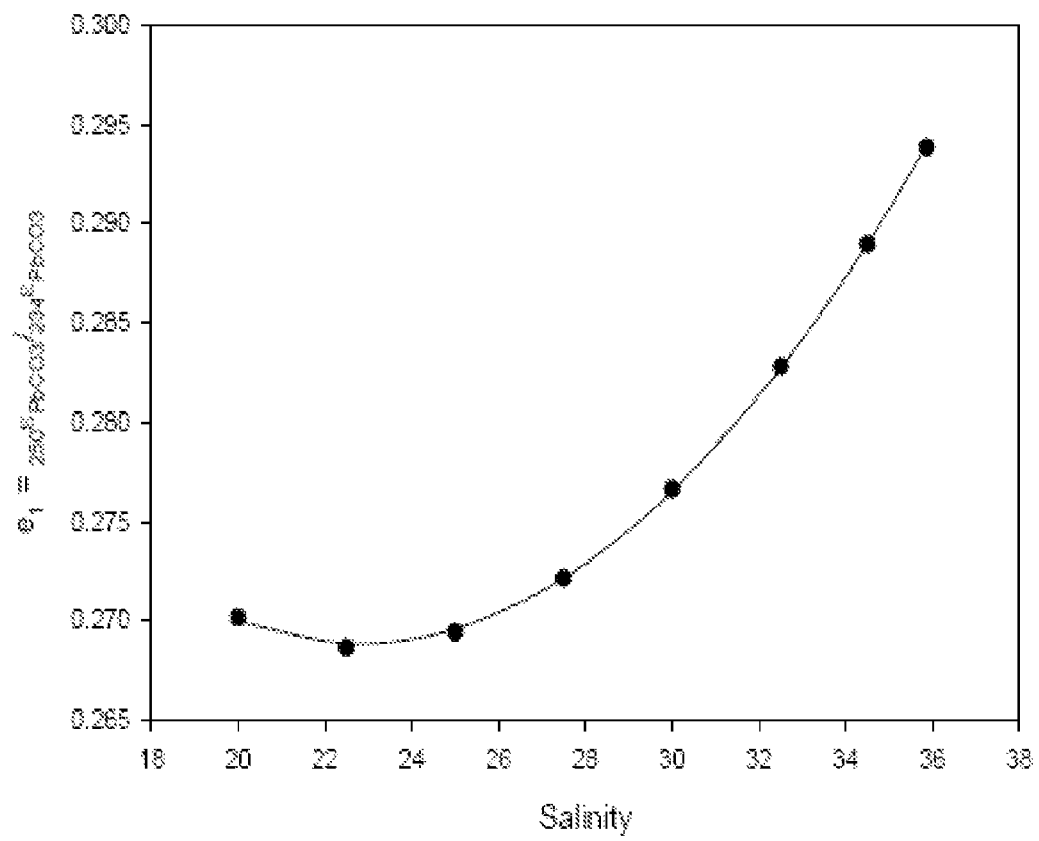
FIG. 7 is a graph showing salinity dependence of $e_1$ at 25° C.
Figure 8:
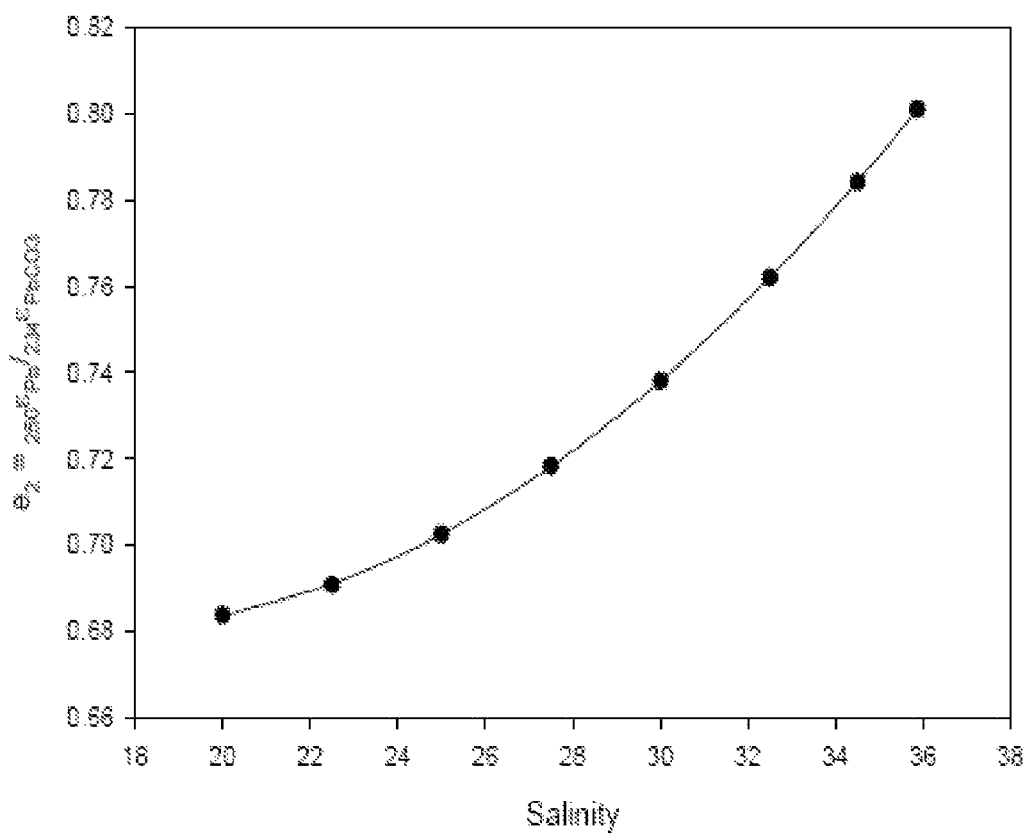
FIG. 8 is a graph showing salinity dependence of $e_2$ at 25° C.
Figure 9:
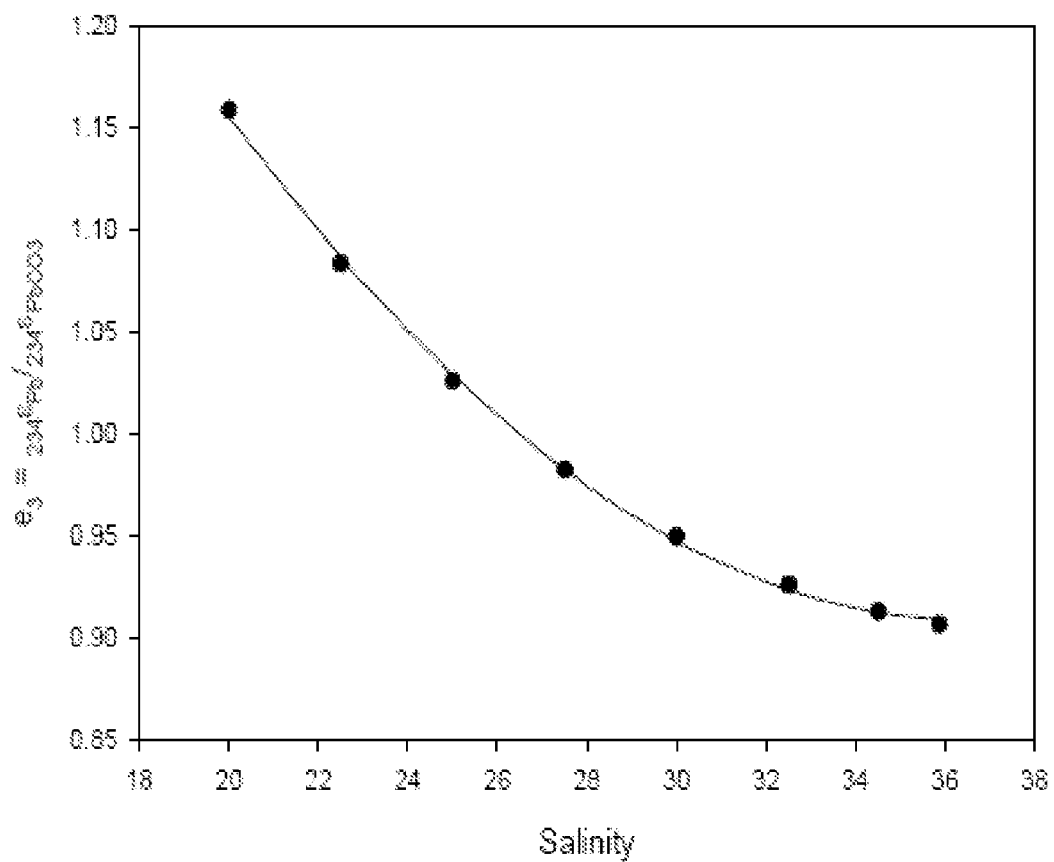
FIG. 9 is a graph showing salinity dependence of $e_3$ at 25° C.

The salinity measurements required for calculations of $\log \{(_{CO3}\beta_1)/(e_2)\}$, $e_1$, and $(e_3/e_2)$ are commonly available from either shipboard or in situ conductimetric measurements. When such is not the case, however, salinity can be calculated using the data that are shown in FIGS. 7-9:

$$S = -8.76 + 45.15R + 6.092R^2 \quad (24)$$

where $R = _{250}A/_{234}A$ and $20 \leq S \leq 36$. The standard deviation for equation (24) estimates of salinity is $\pm 0.06$ salinity units. Thus, equation (24) provides seawater salinity estimates that are precise to approximately 0.2% over the normal salinity range of seawater.

Example 4

Determination of Carbonate Ion Concentration Using Additional Metal Ion Species Inorganic complexation of some ions in seawater, including lead and copper, is strongly dominated by formation of complexes with forms including $PbCO_3^0$ and $CuCO_3^0$. [Byrne, R. H., Inorganic lead complexation in natural seawater determined by UV spectroscopy, *Nature*, (1981) 290:5806, pgs. 487-489; Byrne, R. H and Miller, W. L., Copper (II) carbonate complexation in seawater, *Geochimica et Cosmochimica Acta*, (1985) 49:8; 1837-1844] Furthermore, these complexes equilibrate with their component ions on time scales much less than one second and, importantly, can be monitored spectrophotometrically. For both copper and lead, it had been determined, by spectrophotometric means (ultraviolet spectroscopy), equilibrium constants (K) of the form:

$$K = [MCO_3^0]/([M^{2+}]_T[CO_3^{2-}]_T)$$

where M is $Pb^{2+}$ or $Cu^{2+}$, and brackets denote total concentrations. These findings (spectrophotometric determinations of stability constants (K) for metal complexes) can then be used for inverse calculations leading to rapid direct observations of carbonate ion concentrations in seawater: Spectra of $Pb^{2+}$ or $Cu^{2+}$ in seawater in conjunction with the equilibrium constants described above allow direct calculation of carbonate ion concentrations, $[CO_3^{2-}]_T$. In spite of the desirability of such a capability, the possibility of this mechanism of determination of carbonate ion concentrations has not been noted previously.

Using the procedure outlined above, carbonate ion concentrations can be determined in a rapid profiling mode (in the oceanic water column) through observations of lead or copper absorbance spectra in the ultraviolet. These absorbance measurements can be obtained as absorbance ratios in the same manner as used to achieve pH measurements precise to 0.0004 units (i.e. hydrogen ion concentrations precise to approximately 1/1,000). Rapid spectrophotometric pH measurements in conjunction with rapid carbonate concentration measurements can then be used to comprehensively characterize the marine $CO_2$ system with small, simple, in situ spectrophotometric devices. Spectrophotometric devices are sufficiently simple, relative to alternative technologies, to greatly facilitate carbon system measurements both in the field and in the laboratory. Devices based on the principles outlined above will allow direct determinations of carbonate saturation states, and can do so on time scales commensurate with very rapid profiling of the water column.

Figure 13:
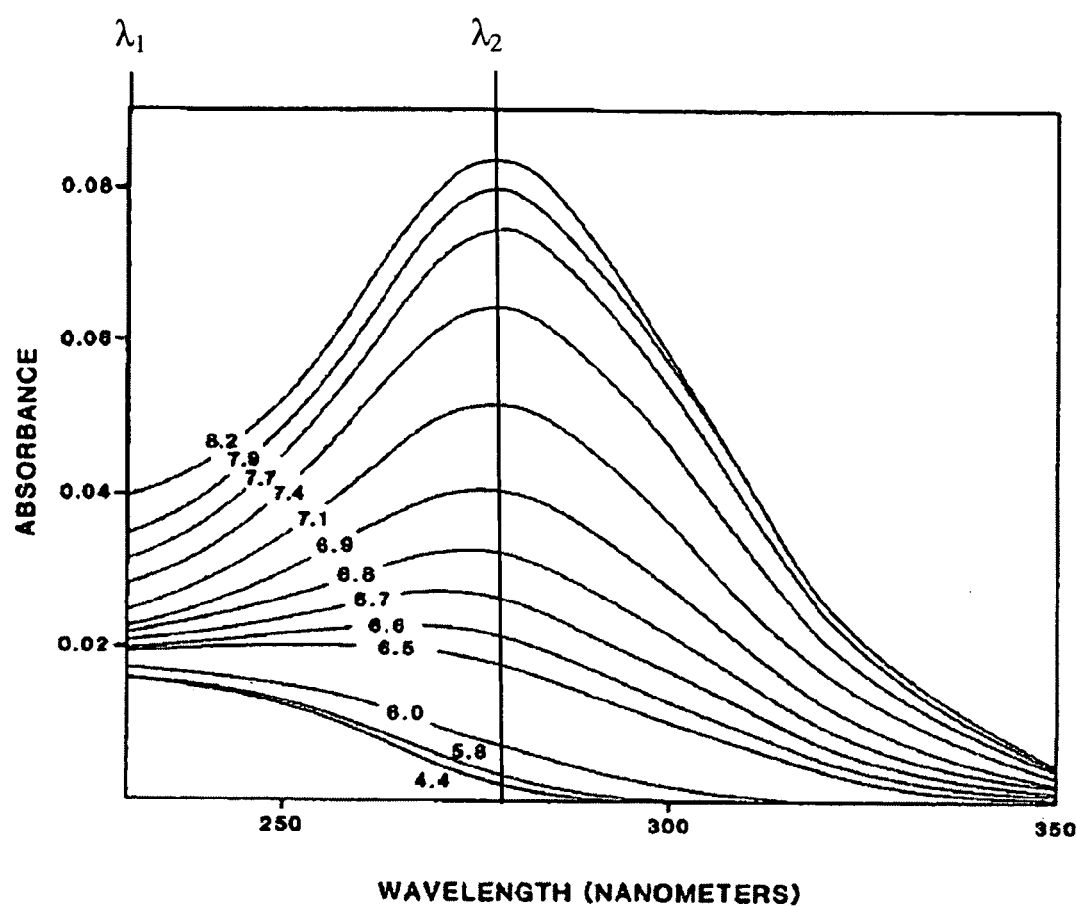
FIG. 13 is a graph showing the absorbance spectra obtained after is $Cu^{II}$ added to seawater to obtain copper concentration on the order of 5 micromolar.

FIG. 13 shows absorbance spectra obtained after copper (II) is added to seawater to obtain copper concentrations on the order of 5 micromolar.

The increase in absorbance with increasing pH, with an absorbance maximum near 280 nanometers, is due nearly entirely to formation of $CuCO_3^0$. This chemical complex is formed via the following reaction:

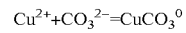

The equilibrium constant for this reaction has been measured in seawater and has the form:

$$K = [CuCO_3^0]/([Cu^{2+}]_T[CO_3^{2-}]_T)$$

In analogy with the use of pH indicators to determine solution pH (where $pH = -\log [H^+]$) via observations of pH-indicator absorbance ratios, the following equation can be used to directly determine a solution's carbonate ion concentration.

$$pCO_3^{2-} = -\log [CO_3^{2-}]_T = \log K + \log \{(R-e_1)/(e_2+Re_3)\}$$

Where K is an equilibrium constant (dependent on temperature, salinity and pressure), $e_i$ are molar absorbances (constants that are very weakly dependent on temperatures, salinity and pressure) and R is a directly measured absorbance ratio ($R = A_2/A_1$) at wavelengths 2 and 1 (i.e. $\lambda_2$ and $\lambda_1$). In the graph shown in FIG. 13, $A_2$ and $A_1$, measured at wavelengths near 280 nanometers and 230 nanometers, are approximately 0.083 and 0.04 at pH=8.2. therefore, at this pH, due predominantly to carbonate complexation, R=2.075. Inspection of The Figure shows that R values at these wavelengths decrease sharply at lower pH (lower carbonate ion concentration). As an example, at pH 4.4, when $[CO_3^{2-}]$ is near zero, R is much smaller than one.

More advanced equations, including equations that consider many wavelengths simultaneously, can be used for this analysis. For greatest accuracy, minor influences can be considered from species such as $CuOH^+$ and $Cu(CO_3)_2^{2-}$.

An advantage of this methodology is that it can be used to directly determine carbonate ion concentrations. Other methods for determining carbonate ion concentrations require measurements of two carbonate system variables plus a subsequent calculation. Thus, the method requires only one type of measurement. Another advantage of this methodology is its speed. Complexation of copper by carbonate ions is essentially instantaneous. Other methods are more laborious and much slower.

It is envisioned that, via in-situ ultraviolet spectrometry, carbonate ion concentrations can be measured directly at a rate of once per second or faster. In conjunction with in-situ measurement of pH, in-situ visible and ultraviolet spectrometry can be used to rapidly and comprehensively characterize the entire $CO_2$ system. The principles involved in this analysis can be used for characterization of many kinds of solutions (i.e. a variety of aqueous media), including blood plasma.

CONCLUSIONS

In the absence of direct spectrophotometric determinations of $[CO_3^{2-}]_T$ as described above, $[CO_3^{2-}]_T$ must be calculated from measurements of either total dissolved inorganic carbon or total alkalinity combined with either pH or $CO_2$ fugacity. While spectrophotometric pH measurements are rapid, with acquisition rates on the order of seconds, measurements of dissolved inorganic carbon, total alkalinity and $CO_2$ fugacity generally require several minutes, as a minimum. Thus, the spectrophotometric procedures for measurements of carbonate ion concentrations described in this work, and those for spectrophotometric pH analysis (Liu et al., 2006), are unique in their suitability for prompt in situ analysis. Spectrophotometric pH and $[CO_3^{2-}]_T$ measurement procedures can also be distinguished from those required for $A_T$, $C_T$ and $f_{CO2}$ with respect to the instrumental simplicity required for the various analyses. In contrast to the procedures and equipment required for analyses of $A_T$, $C_T$ and $f_{CO2}$, spectrophotometers are common equipment items in a wide variety of research and teaching laboratories. As has been the case for spectrophotometric measurements of pH, it should be anticipated that the parameters required for quantitative measurements (e.g., equations 21 through 24) will be amenable to further refinement. It should be emphasized in this case that, through measurements of absorbance ratios, future improvements in $Pb^{II}$ and molar-absorbance-ratio characterizations will allow refinement in $[CO_3^{2-}]_T$ measurement accuracy. As long as data are archived as R—S pairs (i.e., absorbance ratio and salinity), measured at 25° C., all data are suitable for quantitative reassessment. As such, observations of $Pb^{II}$ absorbance ratios provide a molecularly-based index for seawater carbonate ion concentrations.

The procedures described in this work are suitable for rapid, quantitative assessments of calcite and aragonite saturation states in seawater. Since the solubility products of calcite and aragonite in S=35 seawater are approximately $10^{-6.367}$ and $10^{-6.186}$ (Millero, 2007), and the total calcium concentration is 0.0103 at salinity 35, the carbonate ion concentrations for saturation with calcite and aragonite are 41.7 μmol/kg and 63.3 μmol/kg, respectively. Comparison of these concentrations with the $\log_{CO3}\beta_1$ results given by equation 11 ($\log_{CO3}\beta_1$=4.106 at S=35) shows that inorganic $Pb^{II}$ is partitioned equally between $PbCO_3^0$ and lead chloride complexes when $[CO_3^{2-}]_T$=78.3 μmol/kg. Thus, the procedures described in this work are well suited to measurement of $CaCO_3$ saturation states both below and well above the saturation levels of calcite and aragonite.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of directly measuring carbonate ion concentrations in seawater comprising the steps of:
adding a $Pb^{II}$ to a sample of the seawater to produce a sample solution;
spectrophotometrically measuring the absorbance of light passing through the sample solution at a plurality of wavelengths, wherein the ultraviolet absorbance of light is a function of the complexation in the sample solution of the added $Pb^{II}$ with the carbonate ion of the seawater sample;
calculating an absorbance ratio by dividing the absorbance of light at one wavelength by the absorbance of light at a different wavelength; and
computing the carbonate ion concentration in seawater based upon the absorbance ratio of the sample solution at the plurality of wavelengths.

2. The method according to claim 1 wherein the spectrophotometric absorbance measurements are obtained in the ultraviolet range.

3. The method according to claim 1 wherein one of the plurality spectrophotometric absorbance measurements used to calculate the absorbance ratio is measured at about $\lambda$=234 nm.

4. The method according to claim 3 wherein a second of the plurality of spectrophotometric absorbance measurements used to calculate the absorbance ratio is measured at about $\lambda$=240 nm. to about $\lambda$=260 nm.

5. The method according to claim 3 wherein the spectrophotometric absorbance measurements are measured at about $\lambda$=234 nm. and about $\lambda$=250 nm.

6. A method of directly measuring carbonate ion concentrations in an aqueous media comprising the steps of:
adding a metal ion species to a sample of the aqueous media to produce a sample solution;
spectrophotometrically measuring the absorbance of light passing through the sample solution at a plurality of wavelengths, wherein the ultraviolet absorbance of light is a function of the complexation in the sample solution of the added metal ion species with the carbonate ion of the aqueous media;
calculating an absorbance ratio by dividing the absorbance of light at one wavelength by the absorbance of light at a different wavelength; and
computing the carbonate ion concentration in aqueous media based upon the absorbance ratio of the sample solution at the plurality of wavelengths.

7. The method according to claim 6 wherein the metal ion species is selected from the group consisting of $Pb^{II}$ and $Cu^{II}$, yttrium, a lanthanide metal and an actinide metal.

8. The method according to claim 6 wherein the metal ion species is $Pb^{II}$ and the absorbance measurements are obtained as absorbance ratios measured at about $\lambda$=234 and about $\lambda$=250.

9. The method according to claim 6 wherein the aqueous media is seawater.

10. The method according to claim 6 wherein the aqueous media is characterized by salinity.

11. The method according to claim 10 wherein the salinity is between about 20 and about 36.

* * * * *